United States Patent [19]

Wang

[11] Patent Number: 5,292,423

[45] Date of Patent: Mar. 8, 1994

[54] METHOD AND APPARATUS FOR TRACE METAL TESTING

[75] Inventor: Joseph Wang, Las Cruces

[73] Assignee: New Mexico State University Technology Transfer Corp., Las Cruces, ; 61993 10 35 03081994 ZZX None 46 1 1 Bell; Bruce F. Niebling; John 9 20

[21] Appl. No.: 864,942

[22] Filed: Apr. 7, 1992

Related U.S. Application Data

[63] Continuation-in-part of Ser. No. 682,907, Apr. 9, 1991.

[51] Int. Cl.$^5$ ............................................. G01N 27/26
[52] U.S. Cl. ..................... 204/434; 204/412; 204/413
[58] Field of Search ................. 204/413, 434, 412

[56] References Cited

U.S. PATENT DOCUMENTS

| | | | |
|---|---|---|---|
| 3,855,099 | 12/1974 | Matson | 204/195 F |
| 4,003,705 | 1/1977 | Buzza et al. | 23/230 R |
| 4,090,926 | 5/1978 | Matson | 204/1 T |
| 4,545,382 | 10/1985 | Higgins et al. | 128/635 |
| 4,661,210 | 4/1987 | Tenygl | 204/1 T |
| 4,695,555 | 9/1987 | O'Keeffe | 436/150 |
| 4,786,373 | 11/1988 | Saloheimo et al. | 204/1 T |
| 4,804,443 | 2/1989 | Newman et al. | 204/1 T |
| 4,865,992 | 9/1989 | Hach et al. | 436/51 |
| 5,019,515 | 5/1991 | Gisin et al. | 436/52 |
| 5,120,421 | 6/1992 | Glass et al. | 204/412 |
| 5,131,999 | 7/1992 | Gunasingham | 204/411 |

FOREIGN PATENT DOCUMENTS

WO 89/09388 10/1989 PCT Int'l Appl. .

OTHER PUBLICATIONS

J. Electroanal Chem. 12(1966)269–276, S. P. Perrone and K. K. Davenport.
Stewart, "Flow Injection Analysis–New Tool for Old Assays–New Approach to Analytical Measurements" *Analytical Chemistry*, vol. 55, No. 9 (Aug. 1983).
Wang, "Anodic Stripping Voltammetry as an Analytical Tool" *Environ. Sci. Technol.*, vol. 16, No. 2 (1982).
Hilditch, "Disposable Electrochemical Biosensors" *Analyst*, vol. 116 (Dec. 1991).
Oakton ® ElectraScan ®, EC–1 Series sales brochure (Feb. 1991).
Wang, "Anodic Stripping Voltammetry–An Instrumental Analysis Experiment" *Chem. Education*, vol. 60, p. 1074 (Dec. 1983).
Green, "Disposable Single–Use Sensors" *Analytical Proc.*, vol. 28 (Nov. 1991).
Wang, "Mercury=Coated Carbon-Foam Composite Electrodes for Stripping Analysis of Trace Metals" *Amer. Chem Soc.*, vol. 64,(1992).

*Primary Examiner*—John Niebling
*Assistant Examiner*—Bruce F. Bell
*Attorney, Agent, or Firm*—Rod D. Baker; Donovan F. Duggan; Deborah A. Peacock

[57] ABSTRACT

Disclosed are a method and apparatus for trace metal testing using mercury-coated screen printed electrodes. Both voltammetric and potentiometric stripping analysis are used. Sample solutions were tested employing both stirring and non-stirring, as well as aeration and deaeration procedures. Microliter samples suitable for slide mounting were also employed.

46 Claims, 9 Drawing Sheets

POTENTIAL (V)

POTENTIAL (V)

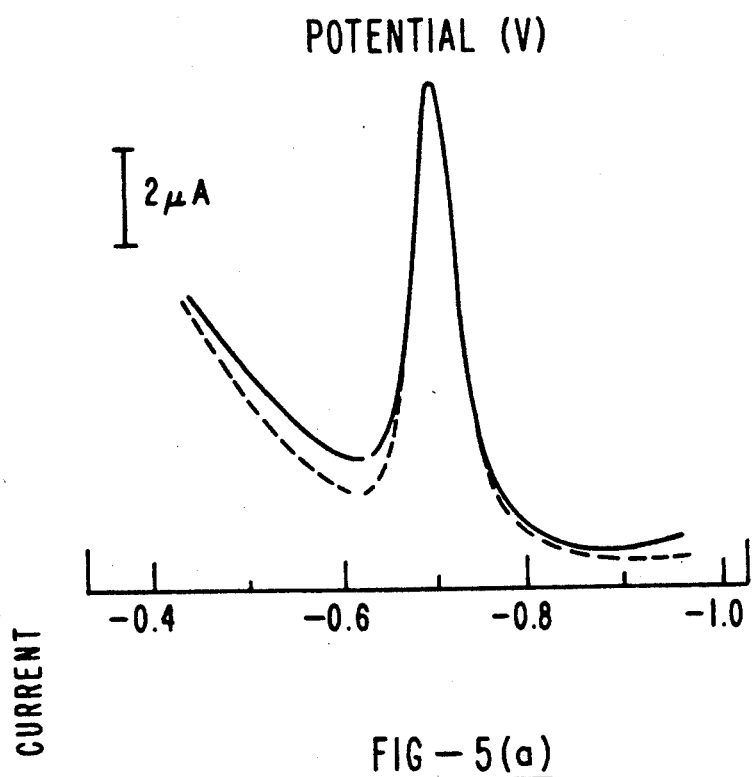
FIG—5(a)
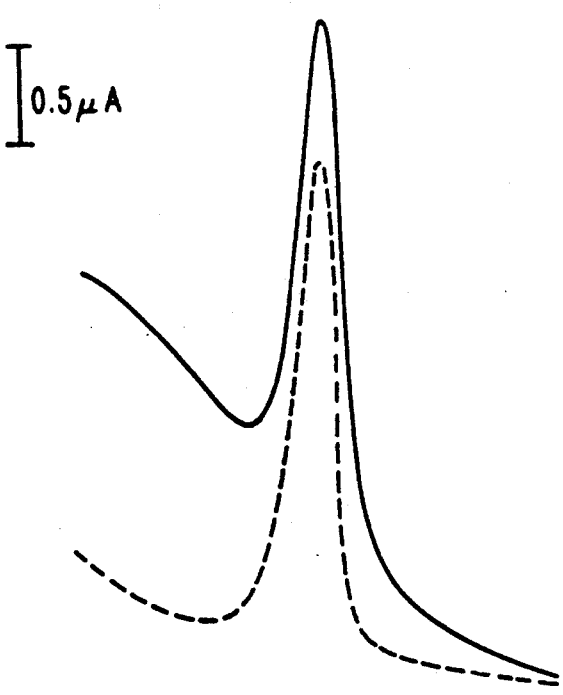
FIG—5(b)

METHOD AND APPARATUS FOR TRACE METAL TESTING

GOVERNMENT RIGHTS

The U.S. Government has a paid-up license in this invention and the right in limited circumstances to require the patent owner to license others on reasonable terms as provided for by the terms of contract No. DE-AC04-76DP00789 awarded by Sandia National Laboratories.

CROSS-REFERENCE TO RELATED APPLICATIONS

This application is a continuation-in-part application of U.S. patent application Ser. No. 07/682,907, entitled Method and Apparatus for Batch Injection Analysis, to Joseph Wang and Ziad Taha, filed on Apr. 9, 1991, the teachings of which are incorporated herein by reference.

BACKGROUND OF THE INVENTION

1. Field of the Invention (Technical Field)

The invention relates to testing apparatus for heavy metals, more particularly disposable, printed electrodes; and a method of using such apparatus.

2. Background Art

Anodic stripping voltammetry (ASV) and potentiometric stripping analysis (PSA) have long been used in trace metal testing, as discussed in "Anodic Stripping Voltammetry as an Analytical Tool" (by Wang Environ. Sci. Technol., Vol 16, No. 2 (1982)) and "Mercury-Coated Carbon-Foam Composite Electrodes for Stripping Analysis of Trace Metals" (by Wang, et al., Analytical Chemistry, Vol. 64, (1992). Anodic stripping voltammetry generally involves the reduction or electrolytic deposition of metals onto an electrode, termed preconcentration, followed by anodically reoxidizing and stripping the metals, thereby producing a plot of current as a function of voltage increasing in amplitude (the measurement step), as discussed in "Anodic Stripping Voltammetry" (by Wang Journal of Chemical Education, Vol. 60, P. 1074).

Normally, ASV and PSA require laboratory conditions for optimum results (see Wang, "Anodic Stripping Voltammetry"). Beakers, nitrogen bubbling equipment, and stirrers are usually required. Electrodes for ASV comprise a working electrode, reference electrode (usually Ag/AgCl), and an auxiliary electrode, usually platinum.

Prior art working electrodes for ASV and PSA, such as those in U.S. Pat. No. 4,804,443, entitled Method and Apparatus for the Determination of Electrochemically Active Components in a Process Stream, to Newman, et al., comprised hanging mercury drop and mercury-coated glassy carbon electrodes. The hanging mercury drop electrode requires laboratory conditions to insure stability and drop size of the drop. As discussed in "Mercury-Coated Carbon-Foam Composite Electrodes for Stripping Analysis of Trace Metals," by Wang, et al., (Analytical Chemistry, Vol 64 (1992)) glassy carbon substrate electrodes also give better results under laboratory conditions.

Two articles entitled "Disposable Single-Use Sensors" and "Disposable Electrochemical Biosensors" (by Monika J. Green and Paul I. Hilditch, MediSense Inc., Units 3 and 4) discuss single-use disposable sensors, also well-known to the prior art. Biosensors, for example, glucose monitors, may comprise a PVC substrate with a working (carbon) and reference (Ag/AgCl) electrodes coated thereon, as well as the enzyme. Such enzyme-coated electrodes are also described in parent application Ser. No. 07/682,907, incorporated herein by reference. Other prior art applications of screen-printed electrodes are electrochemical measurements of ascorbic acid or reduced glutathione.

As disclosed in the parent application, working electrodes, particularly flat or planar carbon paste electrodes, can effectively be modified. Chemical and biological modification involving selective electrode coatings or membranes, are disclosed. Also disclosed in the parent application is the use of optical or thermal devices as sensors.

Parent application Ser. No. 07/682,907, while generally disclosing apparatus and method for batch injection analysis, also used voltammetric and potentiometric measurements and measurement devices therein.

A requirement for decentralized testing of trace metals has evolved. Field or on-site trace metal testing further suggests a need for disposable single-use electrodes. However, despite the ready availability, low cost, and general convenience of screen-printed carbon electrodes, formerly used primarily as biosensors, they are nowhere in the prior art suggested for use in trace metal detection apparatus.

SUMMARY OF THE INVENTION

Disclosure of the Invention

In accordance with the present invention, there is provided a method of analyzing trace metals comprising the steps of providing a plurality of flat printed electrodes, coating at least one of the plurality of flat printed electrodes with mercury, and analyzing a sample for heavy metal content with the plurality of electrodes. The method of the invention further comprises the step of providing at least one flat screen-printed Ag/AgCl reference electrode, and at least one flat screen-printed carbon electrode.

The step of analyzing a sample for heavy metal content comprises the steps of either voltammetrically or potentiometrically analyzing the sample. The preferred method of the invention further comprises the step of preconcentrating the heavy metal upon an electrode.

The preferred method of the invention further comprises the steps of dearating and stirring the sample. The step of analyzing a sample further comprises the step of analyzing a microliter sample solution. The step of analyzing a microliter sample solution further comprises the steps of analyzing urine and analyzing drinking water.

The preferred apparatus of the invention comprises means for providing a plurality of flat printed electrodes, means for coating at least one of said plurality of flat printed electrodes with mercury, and means for analyzing a sample for heavy metal content with said plurality of electrodes. The means for providing a plurality of flat printed electrodes further comprises means for providing at least one flat screen-printed Ag/AgCl reference electrode and at least one flat screen-printed carbon electrode.

The preferred means for analyzing a sample for heavy metal content further comprises means for voltammetrically or potentiometrically analyzing the sample.

The preferred apparatus of the invention further comprises means for preconcentrating the heavy metal upon an electrode and means for deaerating and stirring the sample. The preferred apparatus of the invention further comprises means for analyzing a microliter sample solution, which may be urine or drinking water.

An object of the invention is the provision of disposable single-use electrodes for trace metal detection.

Another object of the invention is the provision of portable, decentralized trace metal detection apparatus.

A further object of the invention is the provision of trace metal testing apparatus effective with microliter samples.

Yet another object of the invention is the provision of inexpensive reusable electrodes for trace metal testing.

An advantage of the present invention is the ease of fabrication and low cost of the electrodes employed.

Another advantage of the invention is the lack of need for stirring and deaeration of samples.

A further advantage of the invention is the highly stable response and low cost attribute of screen-printed carbon electrodes for centralized operations.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIGS. 5(a) and 5(b) show square-wave stripping voltammogram with carbon strip and glassy carbon electrodes, respectively;

DESCRIPTION OF THE PREFERRED EMBODIMENTS

Figure 1A:
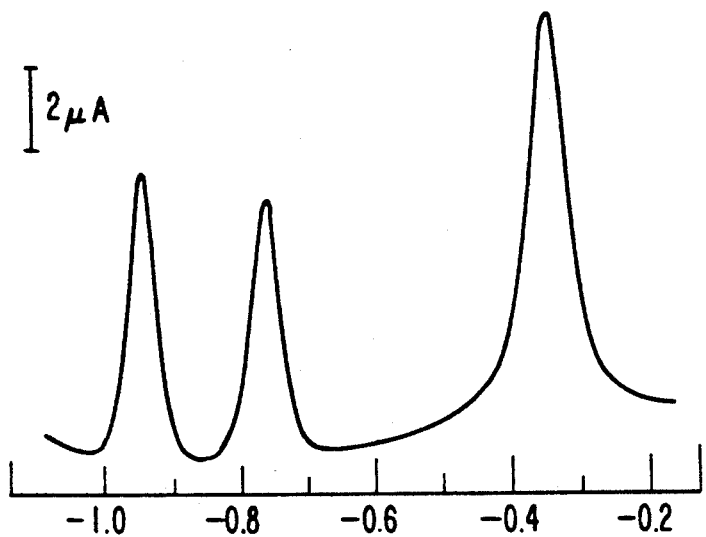
FIGS. 1(a)-1(c) depict voltammograms using a mercury-coated carbon strip electrode, a glassy carbon electrode, and a hanging mercury drop electrode, respectively.

Best Modes for Carrying Out the Invention

Parent application Ser. No. 07/682,907 discloses a plurality of electrodes suitable for use with the batch injection analysis apparatus disclosed therein. Among such electrodes are planar electrodes comprising, for example, carbon paste. Such electrodes may further comprise chemical, enzymatic or ion-selective coatings thereon for voltammetric and potentiometric analyte testing.

The present invention, in common with parent application Ser. No. 07/682,907, employs voltammetric and potentiometric testing for trace metals. Differential pulse stripping voltammograms were obtained with an EG&G PAR 264A voltammetric analyzer, a PAR 303A static mercury-drop electrode, and a PAR 0073 X-Y recorder.

A Tracelab potentiometric stripping unit (PSU 20, Radiometer), with SAM 20 sample station (Radiometer) and an IBM PS/2 55SX, were used to obtain potentiograms. Square-wave stripping voltammograms were obtained with a BAS 100A electrochemical analyzer. Most voltammetric and potentiometric stripping experiments were carried out in 10- and 20-mL cells (BAS and Radiometer), with the electrodes joining through holes in the cover.

The screen-printed electrodes (ExacTech Blood Glucose Strips of Medisense Inc, for example) were purchased. These strips comprise working (carbon) and reference electrodes printed on a PVC substrate (with carbon contacts on the opposite side). One printed carbon contact served as a substrate for the mercury film electrode (since the original working-electrode target area is covered with enzyme/mediator layers). The printed electrode (Ag/AgCl) from another strip served as reference during the voltammetric experiments. Potentiometric stripping work employed the conventional Ag/AgCl electrode of the TraceLab unit. Most experiments employed a platinum wire auxiliary electrode. Some experiments involved a two-electrode system and 100 $\mu$L sample drops. For this purpose, the strip was cut in the center, to allow placing of the carbon contact in direct proximity to the printed reference electrode (on a microscope slide).

All solutions were prepared with double-distilled water. The metal atomic absorption standard solutions (1000 mg/L) were purchased. The supporting electrolyte was an acetate buffer solution (0.02M, pH 4.8). Drinking water samples were collected from laboratory spigots. The urine samples were obtained from a healthy volunteer. Fumed silica was also obtained.

Anodic stripping voltammetry (ASV) and potentiometric stripping analysis (PSA) were performed in the following manner. The mercury film was preplated from a non-deaerated, stirred, 80 mg/L mercury solution (in 0.02M HCl), by holding the carbon strip electrode at the deposition potential ($-1.15$ V for ASV or $-0.90$ V for PSA) for fifteen minutes. The potential was then switched to $-0.20$ V (ASV) or $-0.05$ V (PSA) for a two minute "cleaning" period.

Subsequent ASV and PSA cycles involved the common metal deposition and stripping steps. Experiments were performed with both stirred and unstirred solutions (during the deposition), as well as in the presence and absence of dissolved oxygen. The stripping step was performed with a quiescent solution. In ASV, the potential was scanned (usually with a differential pulse waveform) and stopped at −0.20 V. This potential was maintained for sixty seconds before the next measurement was performed. Potentiometric stripping was carried out by applying a constant oxidation current of +1.0 μA; the electrode was conditioned for fifteen seconds at −0.05 V before the next deposition-stripping cycle. The mercury film was removed by holding it at +0.40 V (vs. the printed reference electrode) for five minutes.

Screen-printed carbon and Ag/AgCl electrodes of disposable glucose strips were employed, as they are readily available, at a very low cost in connection with the ExacTech blood glucose meter. Since the target working electrode area for glucose testing is covered with the enzyme/mediator layer, the carbon contact—on the opposite side of the strip—was successfully used as substrate for the mercury film.

EXAMPLES (INDUSTRIAL APPLICABILITY)

The invention is further illustrated by the following non-limiting examples.

EXAMPLE 1

Figure 1B:
Figure 1C:
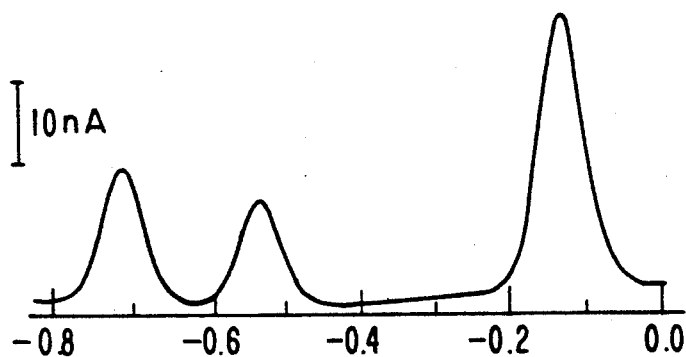

FIG. 1 compares stripping voltammograms for a solution containing 25 μg/L cadmium, 40 μg/L lead, and 35 μg/L copper, obtained under identical conditions at a mercury-coated screen-printed carbon electrode (FIG. 1(a)), a glassy carbon electrode (FIG. 1(b)), and a hanging memory drop electrode (FIG. 1(c)). Further, (a) and (b) used screen-printed Ag/AgCl reference electrodes, while a conventional Ag/AgCl electrode was employed in (c). Preconcentration was for three minutes at −1.15 V with stirred (400 rpm) deaerated solutions. A differential pulse waveform of 10 mV/s scan rate and amplitude of 50 mV was applied. The mercury-coated screen-printed electrode of the invention exhibits well-defined, sharp stripping peaks, good resolution between neighboring signals, low background current, and a wide potential window. A relatively short (three minutes) preconcentration time apparently allows convenient quantitation of μg/L (parts per billion) concentration. Comparison to the traditional hanging mercury drop or glassy carbon electrodes indicates that sensitivity and overall signal-to-background properties are not compromised by the use of the screen-printed carbon substrate electrode of the present invention.

It is further noted that the use of a screen-printed reference Ag/AgCl electrode resulted in approximately a 200 mV negative shift in peak potentials.

Figure 2B:
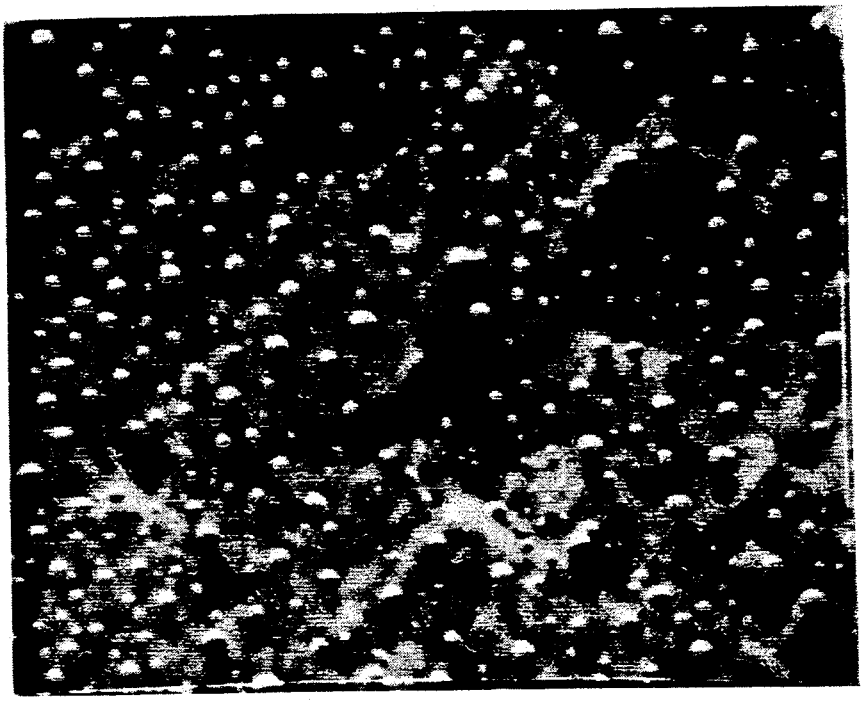
FIGS. 2(a) and 2(b) illustrate bare and mercury coated screen printed carbon electrodes.
Figure 2A:
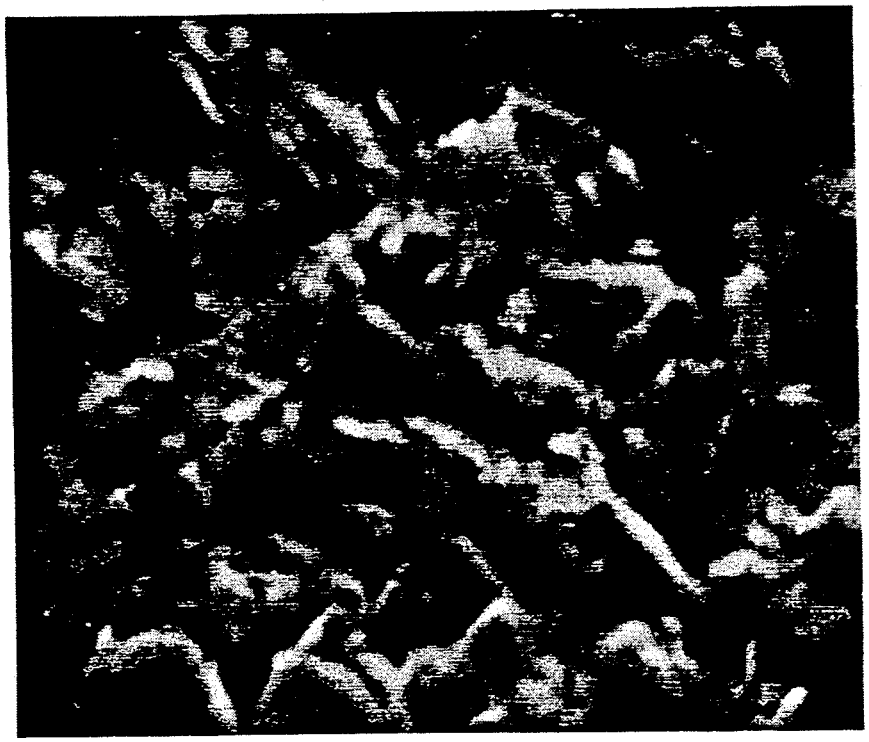

FIGS. 2 depict scanning electron microscopy micrographs of bare (FIG. 2(a)) and mercury-coated screen-printed carbon electrodes (FIG. 2(b)). The bare carbon strip presents some roughness and discontinuity; the mercury deposition (FIG. 2(b)) resulted in numerous spherical microdroplets of 1-2 μm diameter, covering approximately 20% of the area. Under the same plating conditions, different microdistributions of the droplets occur on the carbon strip and glassy carbon electrodes; the strip exhibits a more favorable "array-like" behavior.

The microdistribution of mercury droplets in FIGS. 2 enhances deposition efficiency from quiescent solutions. As a result of the nonlinear diffusional flux to the individual droplets, and the distribution of the droplets, high ratios of current peaks in quiescent (ip,q) and stirred solution (ip,s) are obtained. For example, an ip,q/ip,s value of 0.25 was estimated from the voltammetric stripping response for 30 μg/L lead following three minutes deposition. Analogous measurements at a mercury-coated glassy carbon surface yielded a value of 0.10. Apparently fewer surface sites for mercury plating are available on the carbon strip resulting in enhanced microarray character.

The data of FIGS. 1 was obtained using common stripping conditions (a deaerated solution stirred during the deposition step), decentralized stripping applications will usually require elimination of a nitrogen purge and convection (such as created by stirring) transport.

EXAMPLE 2

Figure 3A:
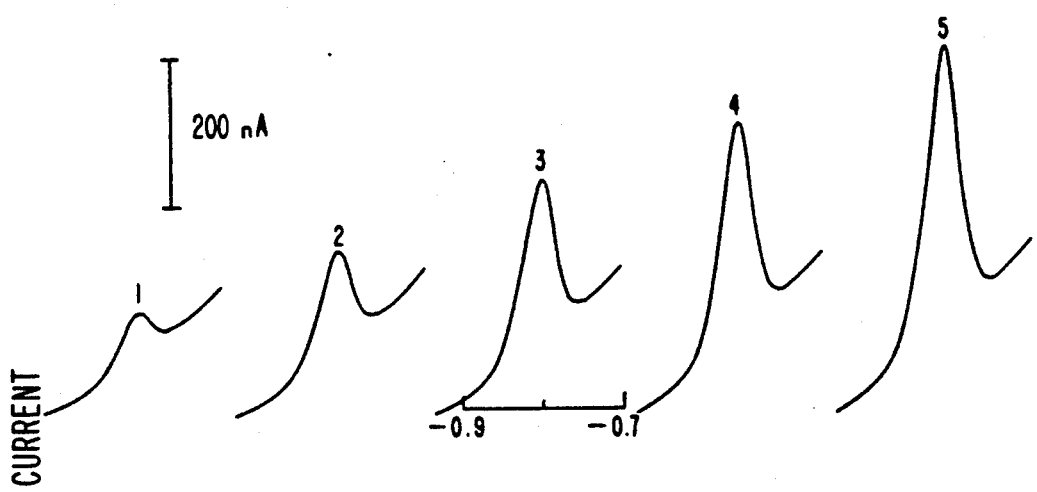
FIGS. 3(a) and 3(b) show voltammograms and potentiograms obtained with incrementally increased lead concentration.
Figure 3B:
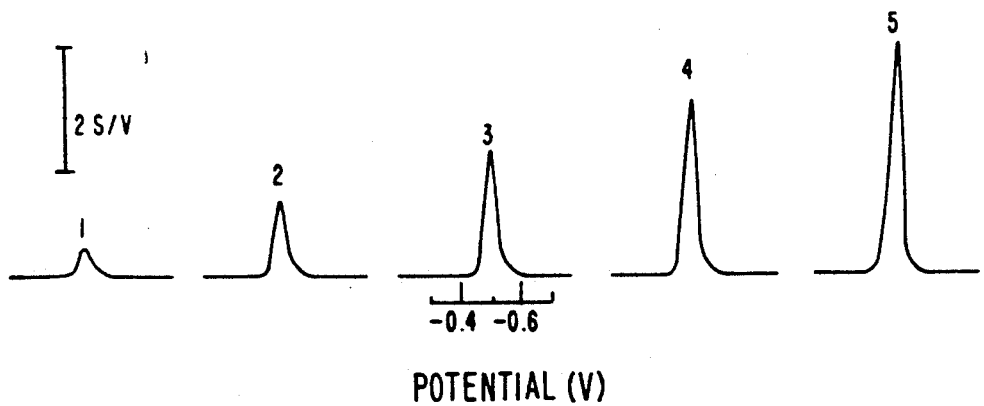

FIGS. 3 illustrate the voltammetric (FIG. 3(a)) and potentiometric (FIG. 3(b)) stripping responses for screen-printed electrodes for quiescent (non-stirred), non-deaerated solution of increasing lead concentration, from 20–100 μg/L (shown as 1–5). Preconcentration was for 120 seconds at −1.15 V for FIG. 3(a) and −0.90 V for FIG. 3(b) with a quiescent non-deaerated solution. Contact current potentiometric stripping was employed at +1.0 μA. Despite these conditions and a short (two minutes) deposition period, well-defined peaks were observed. The five peaks depicted represented part of a series of ten 10 μg/L concentration increments. The calibration plots were linear over the entire range, with slopes of 17 nA·L/μg (FIG. 3(a)), and 1.37 mm$^2$·L/μg (FIG. 3(b)), and a correlation coefficient of 0.999.

The sharper peaks and lower background response of the potentiometric stripping analysis (FIG. 3(b)) make it more attractive under quiescent, non-deaerated conditions.

EXAMPLE 3

Figure 4A:
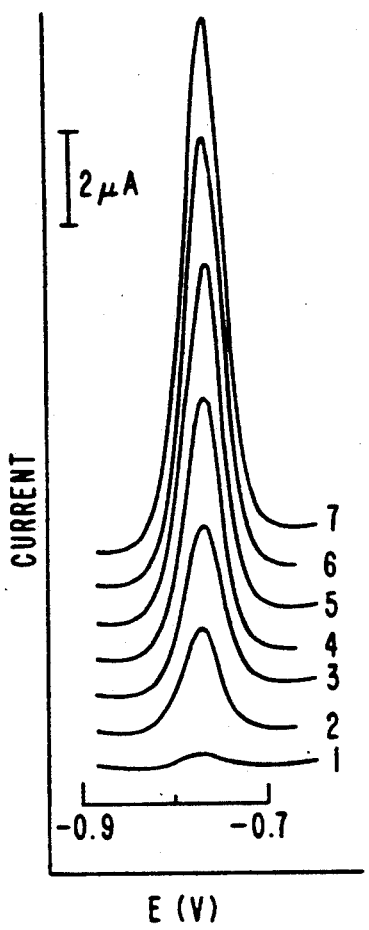
FIGS. 4(a)-4(c) depict voltammetric, potentiometric, and time plots obtained after different preconcentration times.
Figure 4B:
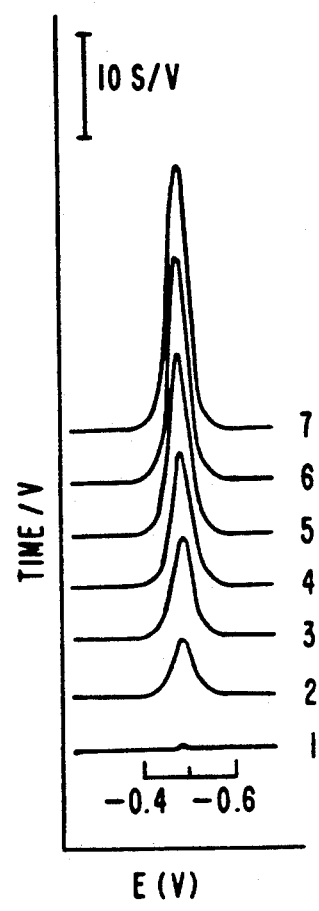

FIGS. 4 illustrate voltammograms (FIG. 4(a)) and potentiograms (FIG. 4(b)) for 50 μg/L lead in the presence of dissolved oxygen in a stirred, non-deaerated solution. Preconcentration was varied (1-7) in 40 second steps from 0 to 240 seconds. The larger the preconcentration period, the larger the response. However, even short preconcentration periods (40-80 seconds) exhibited well-defined peaks.

Figure 4C:
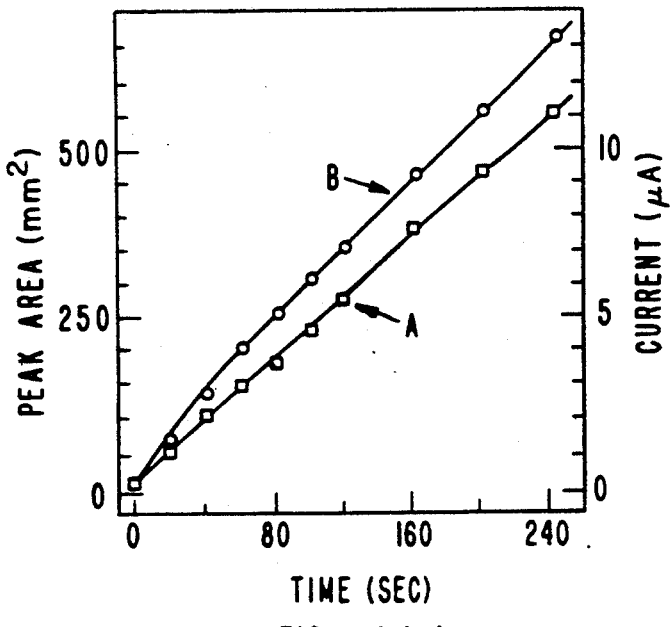

FIG. 4(c) depicts a plot of responses vs. preconcentration time plots. The voltammetric responses exhibit linear dependency while the potentiometric responses showed nonlinear dependency.

Larger preconcentration times allow convenient quantitation of sub-μg/L trace metal concentrations. Detection limits of 30 and 50 ng/L (parts per trillion) lead and cadmium, respectively, were estimated from voltammetric stripping measurements of 1.0 and 0.5 μg/L stirred and deaerated solutions of these metals following ten minutes preconcentrations. Analogous potentiometric stripping measurements of a non-deaerated solution yielded detection limits of 0.3 and 0.4 μg/L lead and cadmium, respectively.

Also evaluated was the effect of deposition potential over a range from −0.60 V to −1.20 V with a two minute deposition time for a non-stirred, non-deaerated 50 μg/L lead solution. The potentiometric response increased gradually between −0.60 V and −1.1 V, then levelled off.

EXAMPLE 4

FIGS. 5 illustrate square-wave stripping voltammograms with a mercury-coated carbon strip (FIG. 5(a) and a glassy carbon electrode (FIG. 5(b) for aerated (solid line) and deaerated (dotted line) solutions containing 30 μg/L lead. Preconcentration was for three minutes at −1.15 V with a stirred solution. The square wave amplitude was 30 mV with steps of 4 mV at a frequency of 30 Hz. The electrolyte was a 0.02M acetate buffer with pH of 4.8. With the screen-printed mercury-coated electrode (FIG. 5(a)), the square-wave responses for both aerated and deaerated solutions were similar. In contrast thereto, the response at the mercury-coated glassy carbon electrode (FIG. 5(b)) clearly indicates a significant oxygen contribution. Apparently, the microarray character of the mercury-coated carbon strip electrode facilitates depletion of oxygen from its surface.

EXAMPLE 5

Figure 6A:
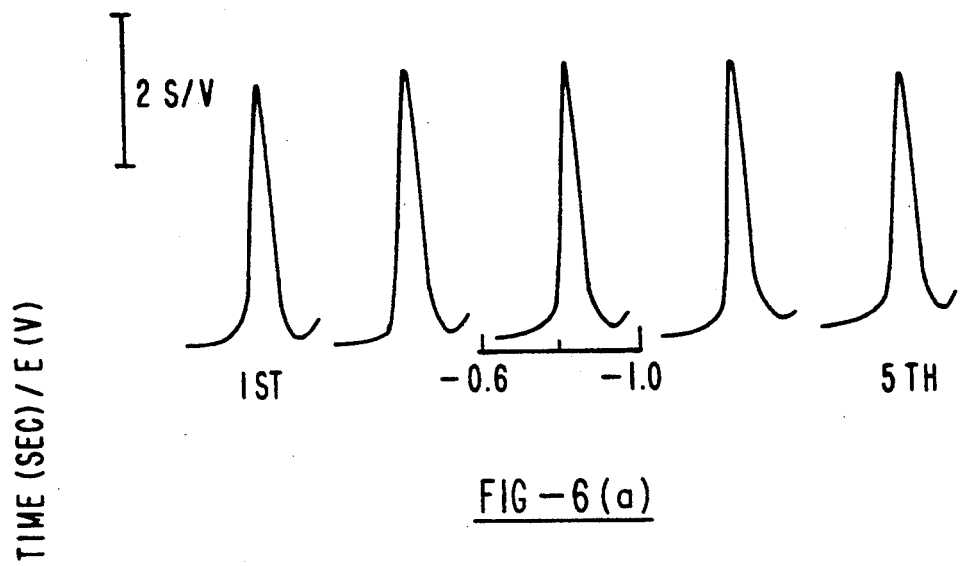
FIGS. 6(a) and 6(b) depict microliter potentiometric analysis in the same sample drop and in different sample drops.
Figure 6B:
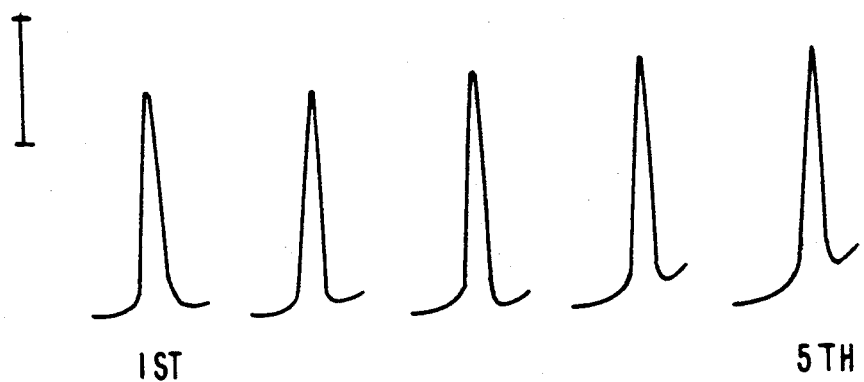

In view of the proposed field and decentralized uses of the preferred embodiment of the invention, microliter vice 10 mL solution stripping analysis, is particularly appropriate. Accordingly, the screen-printed carbon and Ag/AgCl reference electrodes were placed in direct contact on a microscope slide. Repetitive potentiometric stripping measurements of the two-electrode systems, as depicted in FIGS. 6, comprised testing 50 μg/L lead solution in the same 100 μL drop (FIG. 6(a)) and in different drops (FIG. 6(b)). Preconcentration was five minutes at −1.15 V, and the solutions were quiescent and non-deaerated. The current employed was a constant +1.0 μA.

Well-defined peaks were observed despite the non-deaerated, unstirred, low concentration samples. The relative standard deviations for these series were 5.2 (FIG. 6(a)) and 3.9 (FIG. 6(b)). Testing of a three-electrode (not shown) revealed no apparent differences in responses.

EXAMPLE 6

Figures 7A, 7B:
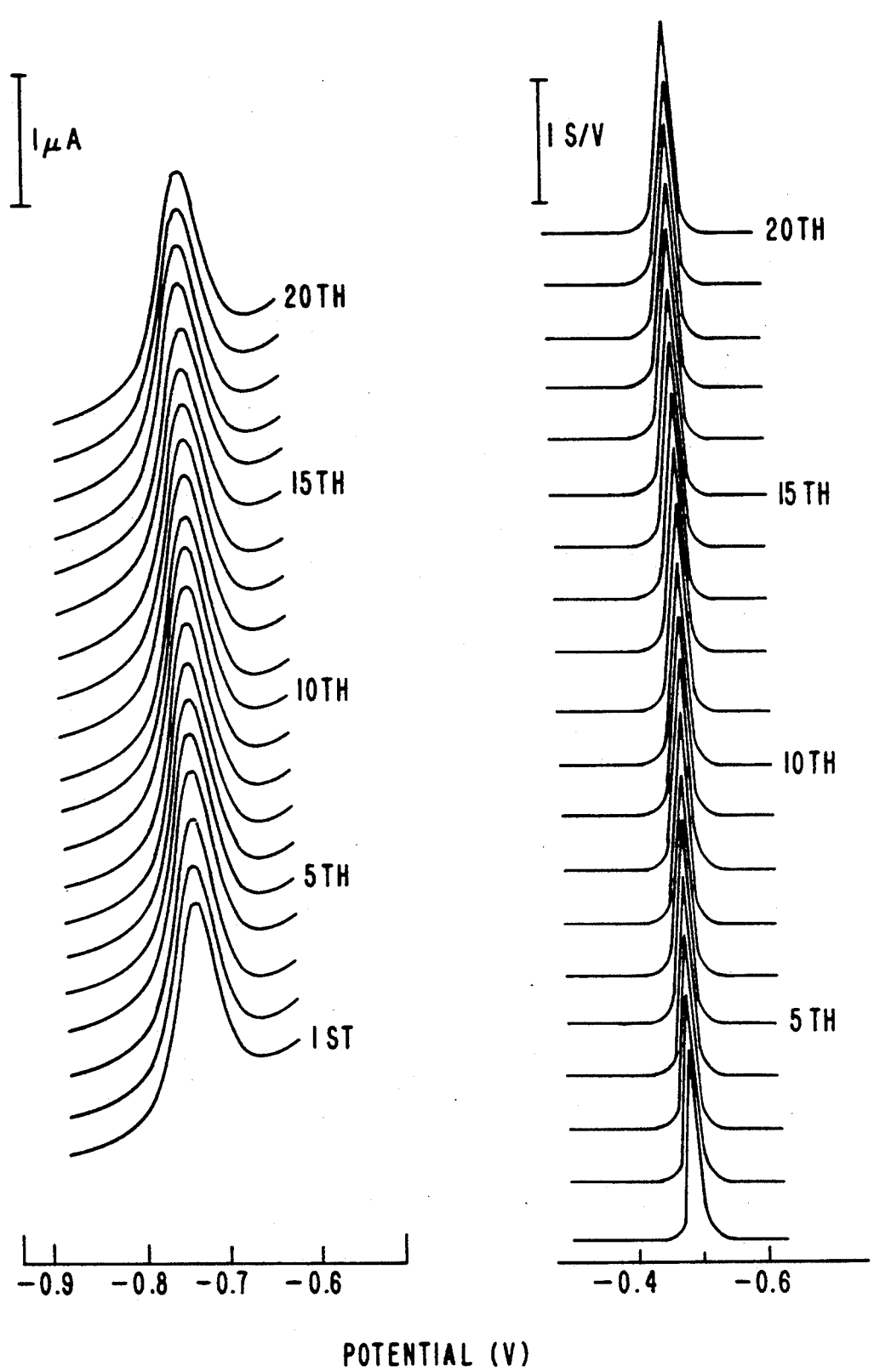
FIGS. 7(a) and 7(b) show voltammograms and potentiograms for repetitive stripping measurements.

Screen-printed electrodes also hold great promise for re-usable applications. FIGS. 7 depict voltammograms (FIG. 7(a)) and potentiograms (FIG. 7(b)) for twenty repetitive stripping measurements of 100 μg/L and 50 μg/L lead solutions, respectively. Preconcentration was 120 seconds with an unstirred, non-deaerated solution.

In both stripping schemes, the peaks remained the same. The relative standard deviation for these series was 2.4% (FIG. 7(a)) and 3.2% (FIG. 7(b)). Again, the potentiometric analysis provided a more favorable response in the presence of oxygen. The stable responses, coupled with the low cost, make screen-printed electrodes an attractive alternative to prior art electrodes.

EXAMPLE 7

Figure 8A:
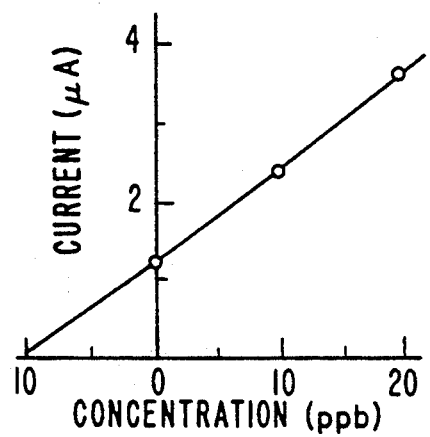
FIGS. 8(a) and 8(b) depict voltammograms after testing urine.

FIGS. 8 and 9 illustrate the applicability of screen-printed electrodes to the analysis of urine and drinking water samples. Voltammograms (FIG. 8(a)) for the urine sample comprised five minutes preconcentration at −1.15 V and pulse amplitude of 25 mV. The solution was deaerated and stirred. Successive concentration increments of 10 μg/L were added. Fumed silica was also added to the sample to "collect" organic surfactants.

Figure 8B:
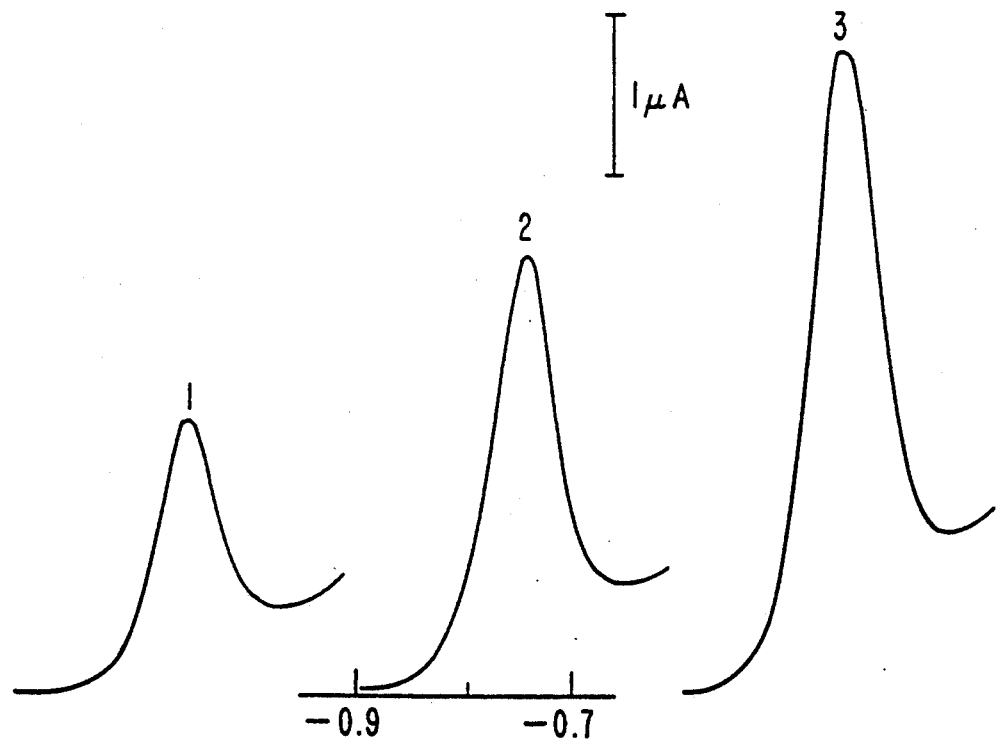
Figure 9A:
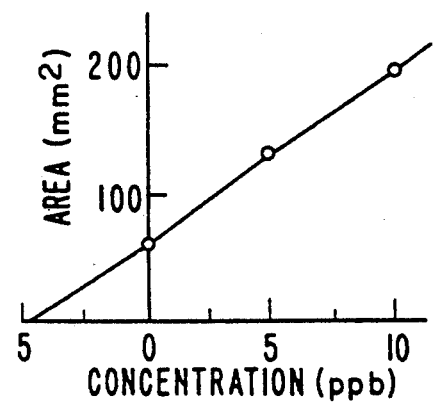
FIGS. 9(a) and 9(b) depict potentiograms after testing drinking water.
Figure 9B:
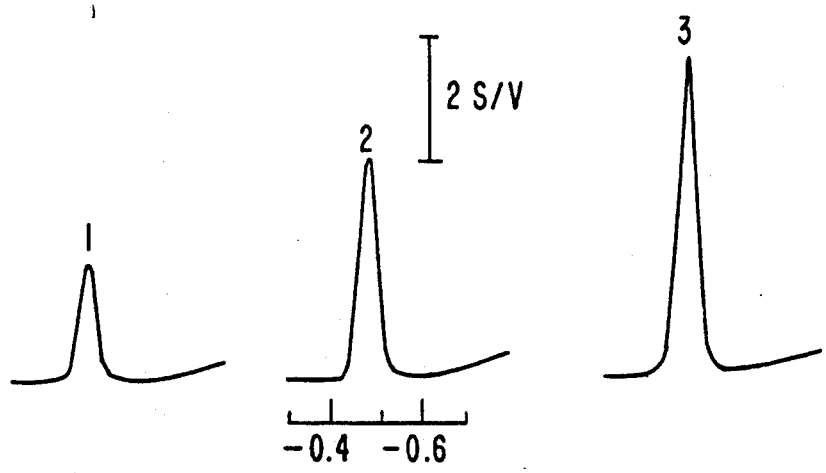

The potentiograms of FIG. 8(b) FIGS. 9(a) and 9(b) were the result of a potentiometric stripping analysis of drinking water. The solution was also stirred but non-deaerated. Successive concentration increments (2,3) of 5 μg/L were added.

In both tests, well-defined peaks resulted. Lead sample values of 10.2 μg/L FIGS. 8 and 4.7 μg/L FIGS. 9 were calculated.

In conclusion, the above results demonstrate for the first time that screen-print electrodes are suitable for stripping measurements of trace metals. These extremely low cost electrodes functions in a manner comparable to traditional stripping electrodes, with no compromise in performance. Neither deoxygenation nor stirring is required; the electrodes hold great potential for decentralized (clinical, environmental, or industrial) testing. These applications will ultimately require the development of small inexpensive portable stripping analyzers. Single-use applications will require complete stripping of the mercury prior to disposal of electrodes. Certain applications, for example, decentralized testing for blood lead level, will require the adaptation of simple and rapid sample preparation, for example, acidification. Additional coverage of electrodes with other layers may also be required.

The preceding examples can be repeated with similar success by substituting the generically or specifically described reactants and/or operating conditions of this invention for those used in the preceding examples.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

I claim:

1. A method of analyzing trace metals comprising the steps of:
   a) providing a plurality of electrodes screen-printed on a substrate;
   b) electrolytically depositing a metal film upon at least one of the plurality of screen-printed electrodes; and
   c) analyzing a sample for heavy metal content by using electrochemical stripping analysis with the plurality of electrodes.

2. The method of claim 1 wherein the step of providing a plurality of screen-printed electrodes further comprises the step of providing at least one reference electrode.

3. The method of claim 2 wherein the step of providing at least one reference electrode further comprises the step of providing a screen-printed Ag/AgCl electrode.

4. The method of claim 1 wherein the step of providing a plurality of screen-printed electrodes further comprises the step of providing at least one screen-printed carbon electrode.

5. The method of claim 1 wherein the step of analyzing a sample for heavy metal content comprises the step of performing anodic stripping voltammetry on the sample.

6. The method of claim 1 wherein the step of analyzing a sample for heavy metal content comprises the step of performing potentiometric stripping analysis on the sample.

7. The method of claim 1 further comprising the step of preconcentrating the heavy metal upon an electrode.

8. The method of claim 1 wherein the step of analyzing a sample for heavy metal content further comprises the step of deaerating the sample.

9. The method of claim 1 wherein the step of analyzing a sample for heavy metal content further comprises the step of stirring the sample.

10. The method of claim 1 wherein the step of analyzing a sample for heavy metal content further comprises the step of analyzing a microliter sample solution.

11. The method of claim 10 wherein the step of analyzing a microliter sample solution comprises the step of analyzing a sample of body fluid.

12. The method of claim 10 wherein the step of analyzing a microliter sample solution comprises the step of analyzing drinking water.

13. Apparatus for heavy metal trace testing comprising:
   means for providing a plurality of electrodes screen-printed on a substrate;
   means for electrolytically depositing a metal film upon at least one of said plurality of screen-printed electrodes; and
   means for analyzing a sample for heavy metal content by electrochemical stripping analysis with said plurality of electrodes.

14. The apparatus of claim 13 wherein said means for providing a plurality of screen-printed electrodes further comprises means for providing at least one reference electrode.

15. The apparatus of claim 14 wherein said means for providing at least one reference electrode further comprises means for providing a screen-printed Ag/AgCl electrode.

16. The apparatus of claim 13 wherein said means for providing a plurality of screen-printed electrodes further comprises means for providing at least one screen-printed carbon electrode.

17. The apparatus of claim 13 wherein said means for analyzing a sample for heavy metal content comprises means for performing anodic stripping voltammetry on the sample.

18. The apparatus of claim 13 wherein said means for analyzing a sample for heavy metal content comprises means for performing potentiometric stripping analysis on the sample.

19. The apparatus of claim 13 further comprising means for preconcentrating said heavy metal upon an electrode.

20. The apparatus of claim 13 wherein said means for analyzing a sample for heavy metal content further comprises means for deaerating said sample.

21. The apparatus of claim 13 wherein said means for analyzing a sample for heavy metal content further comprises means for stirring said sample.

22. The apparatus of claim 13 wherein said means for analyzing a sample for heavy metal content further comprises means for analyzing a microliter sample solution.

23. The apparatus of claim 22 wherein said microliter sample solution comprises a sample of body fluid.

24. The apparatus of claim 22 wherein said microliter sample solution comprises drinking water.

25. The method of claim 1 wherein the step of electrolytically depositing a metal film comprises the step of electrolytically depositing mercury.

26. The method of claim 1 wherein the step of electrolytically depositing a metal film comprises the step of electrolytically depositing a member selected from the group consisting of platinum, silver, and gold.

27. The apparatus of claim 13 wherein said metal film comprises mercury.

28. The apparatus of claim 13 wherein said metal film comprises a member selected from the group consisting of platinum, silver, and gold.

29. The method of claim 7 wherein the step of preconcentrating the heavy metal comprises the step of causing adsorptive accumulation of at least one heavy metal upon said metal film.

30. The apparatus of claim 19 wherein said means for preconcentrating said heavy metal comprises means for causing adsorptive accumulation of at least one heavy metal upon said metal film.

31. The method of claim 11 wherein the step of analyzing a sample of body fluid comprises the step of analyzing a member selected from the group consisting of blood and urine.

32. The apparatus of claim 23 wherein said sample of body fluid comprises a member selected from the group consisting of blood and urine.

33. The method of claim 1 wherein the step of analyzing a sample for heavy metal content further comprises the step of anaylzing a sample of liquid food.

34. The apparatus of claim 13 wherein said means for analyzing a sample for heavy metal content further comprises means for analyzing a sample of liquid food.

35. The method of claim 1 wherein the step of providing a plurality of electrodes further comprises providing a plastic substrate.

36. The apparatus of claim 13 wherein said substrate comprises plastic.

37. A method of analyzing trace metals comprising the steps of:
   a) providing a plurality of electrodes upon a plastic substrate;
   b) electrolytically depositing a metal film upon at least one of the plurality of electrodes; and
   c) analyzing a sample for heavy metal content by using electrochemical stripping analysis with the plurality of electrodes.

38. The method of claim 37 wherein the step of analyzing a sample for heavy metal content comprises the step of performing anodic stripping voltammetery on the sample.

39. The method of claim 37 wherein the step of analyzing a sample for heavy metal content comprises the step of performing potentiometric stripping analysis on the sample.

40. The method of claim 37 wherein the step of analyzing a sample comprises the step of analyzing a sample of body fluid.

41. The method of claim 40 wherein the step of analyzing a sample of body fluid comprises the step of analyzing a member selected from the group consisting of blood and urine.

42. Apparatus for heavy metal trace testing comprising:
   a) means for providing a plurality of electrodes upon a plastic substrate;
   b) means for electrolytically depositing a metal film upon at least one of said plurality of electrodes; and c) means for analyzing a sample for heavy metal content by electrochemical stripping analysis with the plurality of electrodes.

43. The apparatus of claim 42 wherein said means for analyzing a sample for heavy metal content comprises means for performing anodic stripping voltammetery on said sample.

44. The apparatus of claim 42 wherein said means for analyzing a sample for heavy metal content comprises means for performing potentiometric stripping analysis on said sample.

45. The apparatus of claim 42 wherein said means for analyzing said sample comprises means for analyzing a sample of body fluid.

46. The apparatus of claim 45 wherein said means for analyzing a sample of body fluid comprises means for analyzing a member selected from the group consisting of blood and urine.

* * * * *